United States Patent
Ye et al.

(10) Patent No.: US 9,169,360 B2
(45) Date of Patent: Oct. 27, 2015

(54) ALKYL PHOSPHINATE POLYMER AND METHODS FOR PREPARING AND USING THE SAME

(71) Applicant: Shanghai Huihai Chemical Technology Co., Ltd., Shanghai (CN)

(72) Inventors: Jinbiao Ye, Shanghai (CN); Xiangdong Xu, Shanghai (CN)

(73) Assignee: Shanghai Huihai Chemical Technology Co., Ltd., Shanghai (CN)

( * ) Notice: Subject to any disclaimer, the term of this patent is extended or adjusted under 35 U.S.C. 154(b) by 0 days.

(21) Appl. No.: 14/530,672

(22) Filed: Oct. 31, 2014

(65) Prior Publication Data

US 2015/0051328 A1    Feb. 19, 2015

Related U.S. Application Data

(63) Continuation of application No. PCT/CN2012/000989, filed on Jul. 23, 2012.

(30) Foreign Application Priority Data

Jul. 9, 2012   (CN) .......................... 2012 1 0236378

(51) Int. Cl.
| | |
|---|---|
| *C08G 79/04* | (2006.01) |
| *C08K 3/38* | (2006.01) |
| *C08K 5/52* | (2006.01) |
| *C08G 79/02* | (2006.01) |
| *C08K 5/5313* | (2006.01) |
| *C08K 13/02* | (2006.01) |
| *C08K 13/04* | (2006.01) |
| *C08L 77/06* | (2006.01) |
| *C07F 9/30* | (2006.01) |
| *C08L 77/02* | (2006.01) |

(52) U.S. Cl.
CPC ............... *C08G 79/04* (2013.01); *C07F 9/301* (2013.01); *C08G 79/02* (2013.01); *C08K 3/38* (2013.01); *C08K 5/52* (2013.01); *C08K 5/5313* (2013.01); *C08K 13/02* (2013.01); *C08K 13/04* (2013.01); *C08L 77/02* (2013.01); *C08L 77/06* (2013.01); *C08K 2003/387* (2013.01)

(58) Field of Classification Search
CPC ...... C08G 79/04; C08G 79/02; C08K 5/5313; C08K 13/02
USPC .......................................................... 528/398
See application file for complete search history.

(56) References Cited

U.S. PATENT DOCUMENTS

| | | | |
|---|---|---|---|
| 4,180,495 A | 12/1979 | Sandler | |
| 4,208,321 A | 6/1980 | Sandler | |
| 4,208,322 A | 6/1980 | Sandler | |
| 5,647,995 A | 7/1997 | Kneller et al. | |
| 6,569,974 B1 | 5/2003 | Sicken et al. | |
| 6,727,335 B2 | 4/2004 | Sicken et al. | |
| 7,129,320 B2 | 10/2006 | Sicken et al. | |
| 7,348,396 B2 | 3/2008 | Sicken et al. | |
| 2007/0027297 A1* | 2/2007 | Sicken et al. ................. | 528/398 |

FOREIGN PATENT DOCUMENTS

CN        101906117 A    12/2010

* cited by examiner

*Primary Examiner* — John Uselding
(74) *Attorney, Agent, or Firm* — Manni Li; Mei & Mark LLP

(57) ABSTRACT

A process for making an alkyl phosphinate polymer having a formula

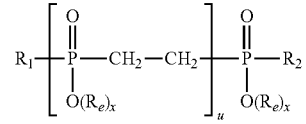

comprising mixing a phosphinic acid or an alkali metal salt of phosphinic acid, a molecular weight modifier, and a polar solvent to form a mixture, adding an alkyne to the mixture, stirring and adding a free radical initiator solution to the mixture, adding the alkyne until saturation, heating and cooling the mixture, and adding to a metallic compound or protonated nitrogen base. The alkyl phosphinate polymer has high heat resistance and is suitable for use in a flame-retardant composition and flame-retardant polymer molding composition.

7 Claims, No Drawings

ALKYL PHOSPHINATE POLYMER AND METHODS FOR PREPARING AND USING THE SAME

CROSS-REFERENCE AND RELATED APPLICATIONS

The subject application is a continuation of PCT international application PCT/CN2012/000989 filed on Jul. 23, 2012, which in turn claims priority on Chinese patent application No. CN 201210236378.2 filed on Jul. 9, 2012. The contents and subject matter of the PCT and Chinese priority applications are incorporated herein by reference.

TECHNICAL FIELD

The present invention relates to an alkyl phosphinate polymer and methods for the preparation and application of the same.

BACKGROUND OF THE INVENTION

The flame retardancy of polyester or nylon may be obtained by mixing with various additives. Generally, halogenated compounds, especially polybrominated aromatic compounds have been used as the flame retardant additives in these types of polymers. It is commonly believed the additive restrains the free radicals reaction in the gas phase of the flame when the product is lit, which makes halogenated flame retardants widely used as the additives for different types polymer material including polyester and nylon. However, in the last 15 years, halogenated flame retardants have been scrutinized on account of ecological concern. Presently, the flame retardant industry is changing towards development of the environment friendly flame retardant additives under the pressure. Phosphorus product is a logical substitute for halogenated flame retardants. In some applications, the phosphorus retardant shows the same high activity with that of halogenated flame retardants, but the phosphorus retardant is rarely used. Most of the phosphorus-containing retardants provide flame retardant activity by condensed-phase reaction, promotion of the polymer carbonization, and char conversion. The effectiveness of the methods obviously depends on the polymer used in connection with the retardant therein. Therefore, phosphorus-containing structure shall be designed as useful for various polymers. In the late 1970s and early 1980s, various salts of diaryl phosphinic acid, alkyl aryl phosphinic acid, or dialkyl phosphinic acid are prepared, such as the aluminum or zinc salt thereof, as shown in U.S. Pat. Nos. 4,180,495; 4,208,321; and 4,208,322, where the phosphinate is added to PET or polymerizes with polyester at 10-20 wt % and the flame retardancy is improved as shown by measuring the Limiting Oxygen Index (LOI).

The addition reaction of alkyne with P—H containing phosphinic acid compound as initiated by the free radical is known: U.S. Pat. No. 5,647,995A discloses the preparation of a series of alkyl phosphinic acid compounds by the reaction. U.S. Pat. No. 6,727,335B2 discloses the preparation of polymerization phosphinic acid with high polymerization degree by using the reaction, and the polymerization route is as follows:

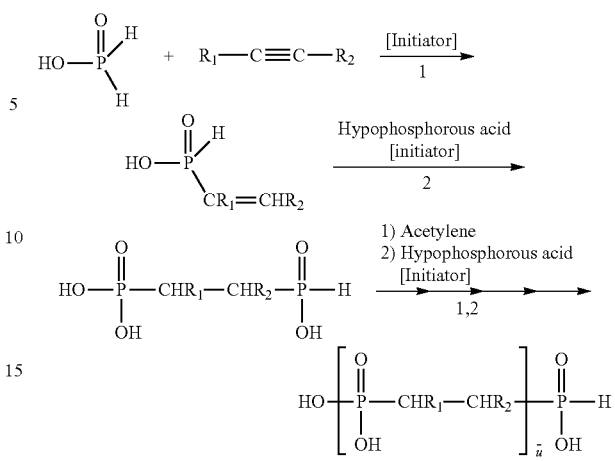

Obviously, the preparation method provides very limited range for the selection of the polymer end group, which is only suitable for an olefin or alkane having 2 carbon atoms or more or H atoms. The effect of the end group on the performance of the polymer may be ignored when the polymerization degree is high; however, for polymers having low polymerization degree, the effect of the end group on the performance of the polymer is great.

SUMMARY OF THE INVENTION

The present invention provides an alkyl phosphinate polymer and the methods of preparation and application thereof. The inventors of the present invention have found that the acidity of polymerized phosphinate is very strong and increases with the increase of the polymerization degree; if it is added to other high-molecular weight polymer material as a flame retardant, the strong acidity will greatly damage the mechanical property of the polymer material, which limits its application. Thus, it is obvious that only polymerized phosphinate with low polymerization degree can be used as the flame retardant. To improve the phosphorus content, research and develop has been devoted to the alkyl hypophosphite of low polymerization degree as the flame retardant for its practical value.

The structure of the alkyl phosphinate polymer of the present invention is as follows:

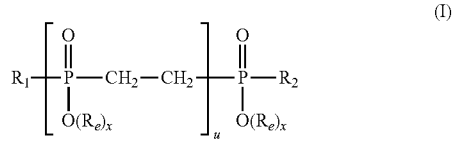

(I)

wherein $R_1$ is a methyl, ethyl, propyl, isopropyl, n-butyl, isobutyl, tertiary butyl, n-amyl group, isoamyl, n-hexyl, isohexyl, hydroxymethyl, or alkoxy;

$R_2$ is a methyl, ethyl, propyl, isopropyl, n-butyl, isobutyl, tertiary butyl, n-amyl group, isoamyl, n-hexyl, isohexyl, hydroxymethyl, or alkoxy;

Re is an alkali metal, alkaline earth metal, transition metal, poor metal, metalloid, lanthanide element, or protonated nitrogen base;

X=1/m, m is the valence of Re.

Preferably, Re is Mg, Ca, Al, Sb, Sn, Ge, Ti, Fe, Zr, Zn, Ce, La, Bi, Sr, Mn, Li, Na, or K, and more preferably, Re is Al, Ca, Ti, Zn, Sn, Zr, or La.

Preferably, the protonated nitrogen base is a proton base having a nitrogen atom with a lone pair electron, and preferably, ammonia, melamine, triethanolamine, particularly, $NH_4'$-melamine, urea, biuret, guanidine, dodecylguanidine, allantoin, guanidine acetate amine, benzoguanamine, tolyl triazole, benzotriazole, 2-amino-4-methylpyrimidine, benzylurea, acetylene urea, glycolylurea, propanediamide amidine, dimethyl urea, diphenyl guanidine, 5,5-diphenyl hydantoin, N,N'-diphenyl urea, glycine anhydride, tetramethyl urea, and their corresponding polymer, such as melamine condensation compound, melem, melam, tripolydicyanamide, or the condensation compound with higher condensation degree;

u represents the degree of polymerization and is an integer in the range of 1 to 6, and preferably, 2 to 5, in the formula. The average degree of polymerization for the polymer is about 1.2 to 6, and preferably, about 2 to 5. The polymerization degree depends on the ratio of the molecular weight modifier and phosphinic acid or phosphinic acid alkali metal salt when the polymer is prepared.

The simplified reaction scheme is as follows:

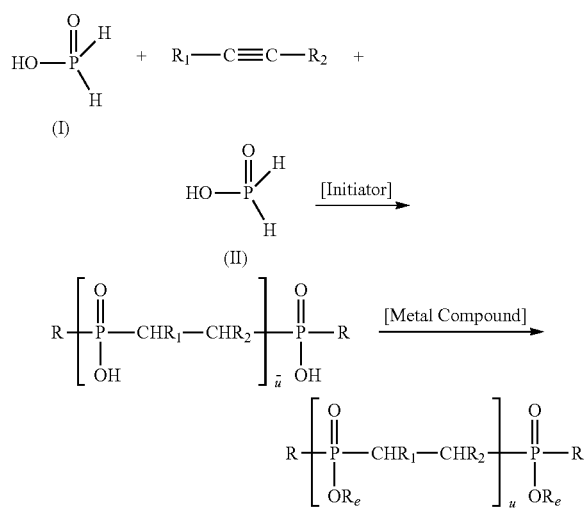

Detailed steps of the method for preparing the alkyl phosphinate polymer of the present invention are as follows:

(1) phosphinic acid or an alkali metal salt of phosphinic acid, a molecular weight modifier, and a polar solvent are mixed and added to a reactor kettle with adjustable pressure. The mixture is heated at 90-110° C. under atmospheric pressure. An alkyne is added to the reaction kettle under the pressure of 3 bar until saturated, wherein the weight ratio of the polar solvent and the solute (i.e., the total weight of the phosphinic acid or the alkali metal salt of the phosphinic acid and the molecular weight modifier) is 4.0-6.0, and the molar ratio of the molecular weight modifier and the phosphinic acid or the alkali metal salt of phosphinic acid is 0.4-9.0.

(2) a free radical initiator solution is continuously stirred and homogeneously added to the mixture of step (1) at 90-110° C., until it reaches saturation. The temperature of the reaction mixture is maintained for 2 to 4 hours, and then, the pressure is adjusted to atmospheric pressure and the temperature is cooled down to 70-80° C. Then, a metallic compound or a protonated nitrogen base is added to react and the temperature of the reaction is maintained for 2-2.5 hours. Then, the solid is separated, washed, and dried to obtain the the product. In the step, the weight of the free radical initiator is 0.5-13% of that of the phosphinic acid or the alkali metal salt of phosphinic acid; the molar amount of the metallic compound or protonated nitrogen base is the molar amount of the phosphinic acid or the alkali metal salt of phosphinic acid divided by m, while m represents the valence of the cation in the metal compound or the protonated nitrogen base.

The metallic compound is a compound of an alkali metal, alkaline earth metal, transition metal, poor metal, metalloid, or lanthanide element.

The free radical initiator solution means that the free radical initiator is dissolved in a polar solvent while the amount of the polar solvent is unlimited so that it is enough to completely dissolved the free radical initiator.

Preferably, the polar solvent for dissolving phosphinic acid or the alkali metal salt of phosphinic acid, molecular weight modifier, and the free radical initiator is water, carboxylic acid, or alcohol, and more preferably, water or acetic acid.

Preferably, the compound of the alkali metal, alkaline earth metal, transition metal, poor metal, metalloid, or lanthanide element is an oxide, hydroxide, hydroxide oxide, sulfate, acetate, nitrate, chloride, or alcoholate.

Preferably, the alkali metal is Li, Na, or K. The alkaline earth metal is Mg, Ca, or Sr. The transition metal is Ti, Fe, Zr, Zn, or Mn. The poor metal is Al, Sn, or Bi. The metalloid is Sb or Ge. The lanthanide element is Ce or La.

More preferably, the compound of Li, Na, K, Mg, Ca, Sr, Ti, Fe, Zr, Zn, Mn, Al, Sn, Bi, Sb, Ge, Ce, or La is an oxide, hydroxide, hydroxide oxide, sulfate, acetate, nitrate, chloride, or alcoholate thereof.

In the present invention, the alkyne used in step (1) is acetylene.

In the present invention, the structure of the molecular weight modifier used in step (1) is as follows:

where:

$R_1$ is an alkyl of $C_1$-$C_6$, aryl, alkoxy of $C_1$-$C_6$, phenoxyl, hydroxyalkyl of $C_1$-$C_6$, hydroxyl, or hydroxyl sodium group;

$R_2$ is an alkyl of $C_1$-$C_6$, aryl, alkoxy of $C_1$-$C_6$, phenoxyl, hydroxyalkyl of $C_1$-$C_6$, hydroxyl, or hydroxyl sodium group;

and $R_1$ and $R_2$ can not be the alkoxy of $C_1$-$C_6$, hydroxyalkyl of $C_1$-$C_6$, hydroxyl, or hydroxyl sodium group at the same time.

Preferably, when $R_1$ is methyl, $R_2$ is methyl or hydroxy; when $R_1$ is ethyl, $R_2$ is ethyl or hydroxyl; when $R_1$ is phenoxyl, $R_2$ is phenoxyl; when $R_1$ is a neopentyl glycol ester, $R_2$ is neopentyl glycol ester; or either $R_1$ or $R_2$ is a hydroxymethyl.

In the present invention, the free radical initiator used in step (2) is an azo compound which is a cationic, anionic, or non-ionic azo compound, inorganic peroxide free radical initiator, or organic peroxide free radical initiator.

Preferably, the cationic azo compound is 2,2'-azobis(2-methylpropionamidine)dihydrochloride (also known as V50); the nonionic azo compound is azobisisobutyronitrile, 4,4'-azobis(4-cyanopentanecarboxylic acid), or 2,2'-azobis(2-methylbutyronitrile); the inorganic peroxide free radical initiator is hydrogen peroxide, ammonium peroxydisulfate, sodium peroxydisulfate, or potassium peroxydisulfate; the organic peroxide free radical initiator is benzoyl peroxide, di-tertbutyl peroxide, or peracetic acid.

The alkyl hypophosphite polymer of the present invention is used as a flame retardant, flame retardant composition, and flame retardant polymer molding composition.

The alkyl phosphinate polymer of the present invention is used as the flame retardant composition as follows: an additive is added to the alkyl phosphinate polymer to get the flame retardant composition, wherein the amount of the alkyl phosphinate polymer is 70-95% weight percentage, the amount of the additive is 5-30% weight percentage. The average particle size of the flame retardant composition is 0.1-3000 µm, preferably 0.1-1000 µm, and more preferably 1-100 µm.

In the present invention, the additive is melamine phosphate, dimelamine phosphate, pentamelamine triphosphate, trimelamine diphosphate, tetramelamine triphosphate, hexakismelamine pentaphosphate, melamine diphosphate, melamine tetraphosphate, melamine pyrophosphate, melamine polyphosphate, melam polyphosphate, melem polyphosphate, or tripolydicyanamide polyphosphate, zinc compound, magnesium compound, calcium compound, aluminum compound, manganese compound, stannum compound, carbodiimide, or (poly)isocyanate. Preferably, the additive is an oligomer ester of tri(hydroxyethyl) isocyanurate and aromatic polycarboxylic acid, benzoguanamine, tri(hydroxyethyl)isocyanurate, allantoin, glycoluril, melamine, melamine cyanurate, urea cyanurate, dicyandiamide, or carbamidine. The carbodiimide is carbonyl caprolactom. The magnesium compound is such as magnesium oxide, magnesium hydroxide, hydrotalcite, layered double hydroxide hydrotalcite, magnesium carbonate, or magnesium calcium carbonate. The calcium compound is calcium hydroxide, calcium oxide, or hydrocalumite. The zinc compound is zinc oxide (such as activated zinc oxide), zinc hydroxide, zinc oxide hydrate, zinc carbonate (such as alkaline zinc carbonate or anhydrous zinc carbonate), zinc stannate, hydroxy zinc stannate, alkaline zinc silicate, alkaline zinc phosphate, alkaline zinc borate, alkaline zinc molybdate, or alkaline zinc sulfite. The aluminum compound is aluminum oxide, aluminum hydroxide, gibbsite, or aluminum phosphate. The manganese compound is manganese oxide or manganese hydroxide. The stannum compound is stannum oxide.

The flame retardant polymer molding composition of the present invention is applied as follows: alkyl phosphinate polymer, polymer, and additive are mixed in the commingler and homogeneously fused in the mixing combination device under certain temperature. The product is protruded and cooled.

In the present invention, the polymer is a derivative of diamine and dicarboxylic acid, and/or aminocarboxylic acid, or a corresponding lactam of polyamide and co-polyamide, such as 2,12-polyamide, 4-polyamide (poly 4-aminobutyric acid), 4,6-polyamide (poly-tetramethylene adipamide), 6-polyamide (polycaprolactam, poly-6-amino caproic acid), 6,6-polyamide (poly(N,N'-hexamethylene adipamide)), 6,9-polyamide (poly(hexamethylene-nonane diacid amide)), 6,10-(poly(hexamethylene decanediamide)), 6,12-polyamide (poly(hexamethylene dodecyldiamide)), 6/6,6-polyamide (poly(hexamethylene hexanamide-co-caprolactam)), 7-polyamide (poly-7-amino-heptylic acid), 7,7-polyamide (poly-heptamethylene pimelic diamide), 8-polyamide (poly-8-amino-octanoic acid), 8,8-polyamide (poly-octamethylene octanoic diamide), 9-polyamide (poly-9-amino-pelargonic acid), 9-polyamide (poly-nonamethylene pelargonate amide), 10-polyamide (poly-10-amino decanoic acid), 10,9-polyamide (poly(decamethylene pelargonate amide)), 10,10-polyamide (poly-decamethylene decyl amide), 11-polyamide (poly-11-amino undecanoic acid), 12-polyamide (poly-lauryl lactam), aromatic polyamide derived from m-xylene, diamine, and adipic acid; polyamide (polyhexamethylene-isophthalamide or polyhexamethylene-terephthalamide) made from hexamethylene diamine and isophthalic acid and/or terephthalic acid, and if suitable, made with an elastomer as a modifier, such as poly 2,4,4-trimethyl hexamethylene terephthalamide or poly-m-phenylene isophthalamide; these polyamide, along with polyolefin, olefin copolymer, ionomer, or chemically bonded or grafted elastomer; or along with polyether, such as a block copolymer of polyethylene glycol, polypropylene glycol, or poly-tetramethylene diol; or a copolyamide or polyamide modified by EPDM or ABS; or condensed polyamide during the treatment process (RIM polyamide system).

The polymer is derived from dicarboxylic acid and diol, and/or hydroxy carboxylic acid, or polyamide of the corresponding lactone, such as polyethylene glycol terephthalate, polybutylene terephthalate (Celanex 2500, Celanex 2002, Celanese; Ultradur, BASF), poly(1,4-dihydroxymethyl cyclohexane terephthalic acid ester), polyhydroxybenzoate, and block poly(ester ether) derived from polyether having hydroxyl end group; and polyester modified by polycarbonate and MBS.

In the present invention, the mixing combination device is a single screw extruder or multi-region screw extruder, and the effective screw length (L) of the extruder (mixing combination device) as represented by the multiplicity of the diameter of the screw D is 4-200D, and preferably 10-50D.

In the present invention, the melting temperature is as follows: the melting temperature of polyethylene glycol terephthalate (PET) is 250-290° C., the melting temperature of polybutylene terephthalate (PBT) is 230-270° C., the melting temperature of 6-polyamide (PA6) is 260-290° C., and the melting temperature of 6,6-polyamide (PA6,6) is 260-290° C.

The production, processing, and testing of the flame retardant plastic molding composition and plastic molding product are as follows.

The flame retardant component and the polymer granules are mixed with the additive as needed, and the mixture is added to the twin-screw extruder under the temperature of 230-260° C. (for making enhanced flame retardant PBT, also known as GRPBT) or 260-280° C. (for making enhanced flame retardant PA66, also known as GRPA 66). The homogenized polymer extrudate is led out and cooled in water bath and then granulated.

After complete drying, the molding combination is processed in the injection molding machine under the melting temperature of 240-270° C. (for GRPBT) or 260-290° C. (for GRPA 66), to get test sample. The test sample having a thickness of 1.6 mm from each combination is tested for UL94 flame class by the "Test for Flammability of Plastic Materials for Parts in Devices and Appliances," which is the plastic flammability standard issued by the Underwriter's Laboratories of America. The flame class under UL94 is as follows:

V0: Afterflame time for each individual specimen t1 or t2 is no more than 10 seconds, the total afterflame time for any condition set is no more than 50 seconds, no fire drops, the specimen is not burn up completely, afterflame plus afterglow time for each individual specimen after second flame application is no more than 30 seconds.

V-1: Afterflame time for each individual specimen t1 or t2 is no more than 30 seconds, the total afterflame time for any condition set is no more than 250 seconds, afterflame plus afterglow time for each individual specimen after second flame application is no more than 60 seconds. other standard as V-0.

V-2: Cotton indicator is lighted by fire drops; other standard as V-1.

Not classified (n.d.): do not satisfy the flame class V-2.

Average degree of polymerization u; use the testing method specified in U.S. Pat. No. 7,129,320B2 by $^{31}$P spectrum.

The flame retardant polymer molding composition of the present invention is suitable for the production of fiber, film, or molded product, especially used in the electrical and electronics field. Preferably, the flame-retardant polymer molded product of the present invention may be used lamp parts, such as lamp holder and lamp bracket, plug and plug-in circuit board, coil frame, shell for the capacitor or contactor, circuit switch, relay shell, and reflector.

The present invention is advantageous in that it provides a highly heat-resistant compound, especially suitable as a flame retardant for glass fiber reinforced polyester and nylon.

DETAILED DESCRIPTION OF THE INVENTION AND EMBODIMENTS

The following detailed description and embodiments serve to explain the principles of the present invention. These examples illustrate the embodiments of the present invention and are not to be construed as limiting the scope of the present invention.

Unless specifically noted, the starting materials are commercially available and as indicated in the below table.

TABLE 1

| | |
|---|---|
| Melamine Pyrophosphate (MPP) | Ciba M200 |
| Polybutylene terephthalate (abbreviated as PBT1) | Celanex 2300GV1/30 (Containing 30% glass fiber) |
| Polybutylene terephthalate (abbreviated as PBT2) | GE 307 |
| Glass fiber | HP3786 (3.2 MM) PFG Fiber Glass Corporation of Taiwan. |
| methyl phosphinic acid diethylester | Shandong Weitian Fine Chemical Industry Technology Co., Ltd. |
| Nylon 66 (PA66) | BASF A3 |
| 2,2-azobenzene-di (2-methyl propyl amidine) dihydrochloride (also known as V50) | Qingdao KeXin New Material Technology Co., Ltd. |
| Zinc borate (ZB) | Ji Qing Chemical Co., Ltd. |

Example 1

Preparation of Molecular Weight Modifier Diethyl Phosphine Oxide

Under the protection of argon, 22 Kg magnesium powder and 250 L dry THF are added to a 2000 L reactor. Then, 3 L bromoethane is added first, stirring is started when the reaction is initiated, and a mixed liquid of 106 Kg bromoethane and 400 L dry THF are added dropwise in a cooling water bath, and keeping the reaction mixture in a slightly boiling state. The reaction is continued for 1 hour at room temperature after the dropwise addition is completed. While being cooled by an ice-water bath, the reaction mixture is added dropwise a liquid mixture of 41.5 Kg diethyl phosphite and 150 L dry THF, and the temperature is controlled under 25° C. The reaction continues for about 4 hours in the 25° C. water bath. Then, the reaction mixture is cooled down by ice-water bath, and potassium carbonate solution which has been cooled to 0° C. is added dropwise (made by dissolving 126.5 Kg potassium carbonate in 150 L water) for hydrolysis. Then, the reaction mixture is filtered, and the solvent in the filtrate is removed by vacuum (50° C., the vacuum degree of circulating water pump is 0.08 MPa) and a yellowish liquid is obtained. The liquid is distilled under the reduced pressure (the vacuum degree of circulating water pump is 0.95 MPa), and the distillate at around 84° C. is collected. The collected colorless and transparent liquid is diethyl phosphine oxide.

Example 2

Preparation of Molecular Weight Modifier Methyl Phosphorous Acid

Hydrochloric acid 100 Kg at 10% concentration is added to a 1000 L enamel reactor under Nitrogen gas, and the temperature is raised to 70-80° C. while 200 Kg methyl phosphorous acid diethylester is continuously added dropwise. After the dropwise addition, the reaction temperature is maintained at 85-90° C. for 1 hour, and then cooled down to room temperature. Hydrochloric acid, ethanol, and water are removed from the mixture via distillation at reduced pressure to obtain a colorless liquid that is methyl phosphinic acid.

Example 3

Preparation of Dialkyl Phosphinic Acid Aluminum Salt Polymer

A mixture containing 15 Kg sodium hypophosphite, 130 Kg molecular weight modifier diethyl phosphine oxide, and 750 Kg deionized water is added to a 2000 L jacketed pressure reactor. Once the temperature of the reaction mixture is heated to 100° C., acetylene is added to the reactor by adjusting valve set at 3 bar until saturation. An aqueous solution of 2.0 Kg potassium persulfate in 200 Kg water is added homogeneously with continuous mixing to the mixture at 100-105° C. The total acetylene consumption is 20.5 Kg. The reaction lasts for 2 hours, the pressure in the reactor is reduced, and the reactor is cooled to 80° C. An aqueous solution of $Al_2(SO_4)_3$ 29 Kg at 50% concentration having 16.53% wt $Al_2O_3$ is added within 2 hours. The solid obtained is centrifuged and washed with water twice, and vacuum dried at 130° C. In the product, u is 1.2, phosphorus content is 26.0%.

Example 4

Preparation of Dialkyl Phosphinic Acid Aluminum Salt Polymer

A mixture of 50 Kg sodium hypophosphite, 100 Kg methyl phosphorous acid, and 700 Kg acetic acid is added to a 2000 L jacketed pressure reactor. Once the reaction mixture is heated to 100° C., acetylene is added to the reactor by adjusting valve set at 3 bar until saturation. An acetic acid solution 2.0 Kg containing 2,2-azobenzene-di(2-methyl propyl amidine)dihydrochloride (also known as V50) is homogeneously added to the mixture under constant stirring at 100-105° C. The total acetylene consumption is 30.1 Kg. The reaction time lasts for 2 hours. Then, the pressure in the reactor is reduced, and the reaction is cooled down to 80° C. An aqueous solution of $Al_2(SO_4)_3$ 350 Kg at 50% concentration having 16.53% wt $Al_2O_3$ is added within 2 hours. The solid obtained is centrifuged and washed with water twice, and vacuum dried at 130° C. In the product, u is 1.7, phosphorus content is 30.3%.

Example 5

Preparation of Dialkyl Phosphinic Acid Aluminum Salt Polymer

A mixture of 80 Kg sodium hypophosphite, 50 Kg methyl phosphorous acid, and 700 Kg acetic acid is added to a 2000 L jacketed pressure reactor. Once the reaction mixture is heated to 100° C., acetylene is added to the reactor by adjusting valve set at 3 bar until saturation. An acetic acid solution 2.0 Kg containing 2,2-azobenzene-di(2-methyl propyl amidine)dihydrochloride (also known as V50) is homogeneously added to the mixture under constant stirring at 100-105° C. The total acetylene consumption is 30.1 Kg. The reaction time lasts for 2 hours. Then, the pressure in the reactor is reduced, and the reaction is cooled down to 80° C. An aqueous solution of $Al_2(SO_4)_3$ 285 Kg at 50% concentration having 16.53% wt $Al_2O_3$ is added within 2 hours. The solid obtained is centrifuged and washed with water twice, and vacuum dried at 130° C. In the product, u is 3.4, phosphorus content is 30.3%.

Example 6

Preparation of Dialkyl Phosphinic Acid Calcium Salt Polymer

A mixture of 80 Kg sodium hypophosphite, 50 Kg methyl phosphorous acid, and 700 Kg acetic acid is added to a 2000 L jacketed pressure reactor. Once the reaction mixture is heated to 100° C., acetylene is added to the reactor by adjusting valve set at 3 bar until saturation. An acetic acid solution 2.0 Kg containing 2,2-azobenzene-di(2-methyl propyl amidine)dihydrochloride (also known as V50) is homogeneously added to the mixture under constant stirring at 100-105° C. The total acetylene consumption is 30.1 Kg. The reaction time lasts for 2 hours. Then, the pressure in the reactor is reduced, and the reaction is cooled down to 80° C. An aqueous solution of $CaCl_2$ 191 Kg at 40% concentration is added within 2 hours. The solid obtained is centrifuged and washed with water twice, and vacuum dried at 130° C. In the product, u is 3.0, phosphorus content is 27.2%.

Example 7

Preparation of Dialkyl Phosphinic Acid Lanthanum Salt Polymer

A mixture of 80 Kg sodium hypophosphite, 50 Kg methyl phosphorous acid, and 700 Kg acetic acid is added to a 2000 L jacketed pressure reactor. Once the reaction mixture is heated to 100° C., acetylene is added to the reactor by adjusting valve set at 3 bar until saturation. An acetic acid solution 2.0 Kg containing 2,2-azobenzene-di(2-methyl propyl amidine)dihydrochloride (also known as V50) is homogeneously added to the mixture under constant stirring at 100-105° C. The total acetylene consumption is 30.1 Kg. The reaction time lasts for 2 hours. Then, the pressure in the reactor is reduced, and the reaction is cooled down to 80° C. An aqueous solution of $LaCl_3 \cdot 6H_2O$ 325 Kg at 50% concentration is added within 2 hours. The solid obtained is centrifuged and washed with water twice, and vacuum dried at 130° C. In the product, u is 3.1, phosphorus content is 22.0%.

Example 8

Preparation of Dialkyl Phosphinic Acid Zinc Salt Polymer

A mixture of 80 Kg sodium hypophosphite, 25 Kg methyl phosphorous acid, 35 Kg diphenyl phosphite, and 600 Kg acetic acid is added to a 2000 L jacketed pressure reactor. Once the reaction mixture is heated to 90° C., acetylene is added to the reactor by adjusting valve set at 3 bar until saturation. An acetic acid solution 2.2 Kg containing 2,2-azobenzene-di(2-methyl propyl amidine)dihydrochloride (also known as V50) is homogeneously added to the mixture under constant stirring at 90° C. Acetylene is continuously added to the mixture until saturation. The total acetylene consumption is 27.5 Kg. The temperature is maintained for 3 hours, then, the pressure in the reactor is reduced, and the reaction is cooled down to 80° C. An aqueous solution of $ZnSO_4 \cdot 7H2O$ 310 Kg at 50% concentration is added. The temperature is maintained for 2 hours. The solid obtained is centrifuged and washed with water twice, and vacuum dried at 130° C. In the product, u is 3.9, phosphorus content is 22.0%.

Example 9

Preparation of Dialkyl Phosphinic Acid Cerium Salt Polymer

A mixture of 80 Kg sodium hypophosphite, 50 Kg methyl phosphorous acid, and 600 Kg acetic acid is added to a 2000 L jacketed pressure reactor. Once the reaction mixture is heated to 90° C., acetylene is added to the reactor by adjusting valve set at 3 bar until saturation. An aqueous solution 3.0 Kg containing ammonium persulfate is homogeneously added to the mixture under constant stirring at 90° C. The total acetylene consumption is 30.0 Kg. The reaction time lasts for 4 hours. Then, the pressure in the reactor is reduced, and the reaction is cooled down to 70° C. An aqueous solution of $CeCl_3$ 177 Kg at 50% concentration is added and the temperature is maintained for 2.5 hours. The solid obtained is centrifuged and washed with water twice, and vacuum dried at 130° C. In the product, u is 3.3, phosphorus content is 22.6%.

Example 10

Preparation of Dialkyl Phosphinic Acid Aluminum Salt Polymer

A mixture of 80 Kg sodium hypophosphite, 70 Kg diphenyl phosphite, and 700 Kg acetic acid is added to a 2000 L jacketed pressure reactor. Once the reaction mixture is heated to 100° C., acetylene is added to the reactor by adjusting valve set at 3 bar until saturation. An acetic acid solution 2.0 Kg containing 2,2-azobenzene-di(2-methyl propyl amidine)dihydrochloride (also known as V50) is homogeneously added to the mixture under constant stirring at 100-105° C. The total acetylene consumption is 30.1 Kg. The reaction time lasts for 2 hours. Then, the pressure in the reactor is reduced, and the reaction is cooled down to 80° C. An aqueous solution of $Al_2(SO_4)_3$ 155 Kg at 50% concentration having 16.53% wt $Al_2O_3$ is added within 2 hours. The solid obtained is centrifuged and washed with water twice, and vacuum dried at 130° C. In the product, u is 6.0, phosphorus content is 21.3%.

Example 11

Preparation of Dialkyl Phosphinic Acid Aluminum Salt Polymer

A mixture of 80 Kg sodium hypophosphite, 25 Kg methyl phosphorous acid, 35 Kg diphenyl phosphite, and 600 Kg acetic acid is added to a 2000 L jacketed pressure reactor. Once the reaction mixture is heated to 100° C., acetylene is added to the reactor by adjusting valve set at 3 bar until saturation. An acetic acid solution 2.0 Kg containing 2,2-azobenzene-di(2-methyl propyl amidine)dihydrochloride (also known as V50) is homogeneously added to the mixture under constant stirring at 100-105° C. The total acetylene consumption is 27.1 Kg. The reaction time lasts for 2 hours. Then, the pressure in the reactor is reduced, and the reaction is cooled down to 80° C. An aqueous solution of $Al_2(SO_4)_3$ 220 Kg at 50% concentration having 16.53% wt $Al_2O_3$ is added within 2 hours. The solid obtained is centrifuged and washed with water twice, and vacuum dried at 130° C. In the product, u is 4.2, phosphorus content is 25.7%.

Example 12

UL94 Test

According to the general description of the "Producing, processing, and testing of the plastic molding product and flame retardant plastic molding composition" as mentioned above, a flame retardant plastic molding composition is produced by a mixture of 14% wt product of Example 3, 6% wt MPP, and 80% wt polybutylene terephthalate (PBT1) mixed by a twin-screw extruder at 230° C. to 260° C. After drying, the flame retardant polymer molding product is obtained by treating the molding composition in an injection molding machine under the melting temperature of 240° C. to 270° C. The grade of the test specimen is V-0 according to UL94 test

Example 13

UL94 Test

According to the general description of the "Producing, processing, and testing of the plastic molding product and flame retardant plastic molding composition" as mentioned above, a flame retardant plastic molding composition is produced by a mixture of 14% wt product of Example 4, 6% wt MPP, and 80% wt polybutylene terephthalate (PBT1) mixed by a twin-screw extruder at 230° C. to 260° C. After drying, the flame retardant polymer molding product is obtained by treating the molding composition in an injection molding machine under the melting temperature of 240° C. to 270° C. The grade of the test specimen is V-0 according to UL94 test.

Example 14

UL94 Test

According to the general description of the "Producing, processing, and testing of the plastic molding product and flame retardant plastic molding composition" as mentioned above, a flame retardant plastic molding composition is produced by a mixture of 14% wt product of Example 5, 6% wt MPP, 50% wt polybutylene terephthalate (PBT2), and 30% wt glass fiber mixed by a twin-screw extruder at 230° C. to 260° C. After drying, the flame retardant polymer molding product is obtained by treating the molding composition in an injection molding machine under the melting temperature of 240° C. to 270° C. The grade of the test specimen is V-0 according to UL94 test.

Example 15

UL94 Test

According to the general description of the "Producing, processing, and testing of the plastic molding product and flame retardant plastic molding composition" as mentioned above, a flame retardant plastic molding composition is produced by a mixture of 14% wt product of Example 10, 6% wt MPP, 50% wt polybutylene terephthalate (PBT2), and 30% wt glass fiber mixed by a twin-screw extruder at 230° C. to 260° C. After drying, the flame retardant polymer molding product is obtained by treating the molding composition in an injection molding machine under the melting temperature of 240° C. to 270° C. The grade of the test specimen is V-1 according to UL94 test.

Example 16

UL94 Test

According to the general description of the "Producing, processing, and testing of the plastic molding product and flame retardant plastic molding composition" as mentioned above, a flame retardant plastic molding composition is produced by a mixture of 14% wt product of Example 11, 6% wt MPP, and 80% wt polybutylene terephthalate (PBT2) mixed by a twin-screw extruder at 230° C. to 260° C. After drying, the flame retardant polymer molding product is obtained by treating the molding composition in an injection molding machine under the melting temperature of 240° C. to 270° C. The grade of the test specimen is V-0 according to UL94 test.

Example 17

UL94 Test

According to the general description of the "Producing, processing, and testing of the plastic molding product and flame retardant plastic molding composition" as mentioned above, a flame retardant plastic molding composition is produced by a mixture of 12% wt product of Example 4, 5% melamine polyphosphate, 1% wt zinc borate, 52% wt polyamide PA66, and 30% wt glass fiber mixed by a twin-screw extruder at 260° C. to 280° C. After drying, the flame retardant polymer molding product is obtained by treating the molding composition in an injection molding machine under the melting temperature of 260° C. to 300° C. The grade of the test specimen is V-0 according to UL94 test.

Example 18

UL94 Test

According to the general description of the "Producing, processing, and testing of the plastic molding product and flame retardant plastic molding composition" as mentioned above, a flame retardant plastic molding composition is produced by a mixture of 14% wt product of Example 7, 5% wt MPP, 1% wt aluminum phosphate, and 80% wt polybutylene terephthalate (PBT1) mixed by a twin-screw extruder at 230° C. to 260° C. After drying, the flame retardant polymer molding product is obtained by treating the molding composition in an injection molding machine under the melting temperature of 240° C. to 270° C. The grade of the test specimen is V-1 according to UL94 test.

The results of the UL94 test examples are summarized in Table 2.

TABLE 2

Results of Examples for UL94 Test.

| Example | 12 | 13 | 14 | 15 | 16 | 17 | 18 |
|---|---|---|---|---|---|---|---|
| Product of Example 3 | 14 | | | | | | |
| Product of Example 4 | | 14 | | | | 12 | |
| Product of Example 5 | | | 14 | | | | |
| Product of Example 7 | | | | | | | 14 |
| Product of Example 10 | | | | 14 | | | |
| Product of Example 11 | | | | | 14 | | |
| ZB | | | | | | 1 | |
| MPP | 6 | 6 | 6 | 6 | 6 | 5 | 5 |
| Aluminum phosphate | | | | | | | 1 |
| PBT1 | 80 | 80 | | | | | 80 |
| PBT2 | | | 50 | 80 | 80 | | |
| Glass fiber | | | 30 | | | 30 | |
| PA6,6 | | | | | | 52 | |
| UL94 | V0 | V0 | V0 | V1 | V0 | V0 | V1 |

Without departing from the scope and subject matter of the present invention, one of ordinary skill in the art may combine or modify various technical features and solutions of the present invention within the scope thereof.

We claim:

1. A process for preparing the alkyl phosphinate polymer, comprising
   mixing a phosphinic acid or an alkali metal salt of phosphinic acid, a molecular weight modifier, and a polar solvent to form a mixture and adding the mixture to an adjustable reactor and heating a temperature of the mixture to 90 to 110° C.,
   adding an alkyne to the adjustable reactor under a pressure of 3 bar,
   continuously stirring a free radical initiator solution homogeneously and adding the free radical initiator solution to the mixture under a temperature of 90 to 110° C.,
   continuing to add the alkyne until the alkyne reaches saturation,
   maintaining the temperature for 2~4 hours and adjusting pressure to atmospheric pressure,
   cooling the mixture to 70-80° C. and adding a metallic compound or protonated nitrogen base to the mixture, while keeping temperature at 70-80° C. for 2-2.5 hours, and
   separating, washing and drying a solid in the mixture to obtain a product having a formula of

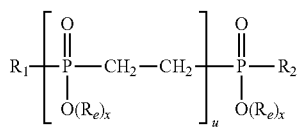

wherein $R_1$ is a methyl, ethyl, propyl, isopropyl, n-butyl, isobutyl, tertiary butyl, n-amyl group, isoamyl, n-hexyl, isohexyl, hydroxymethyl, or alkoxy;
$R_2$ is a methyl, ethyl, propyl, isopropyl, n-butyl, isobutyl, tertiary butyl, n-amyl group, isoamyl, n-hexyl, isohexyl, hydroxymethyl, or alkoxy;
$R_e$ is an alkali metal, alkaline earth metal, transition metal, poor metal, metalloid, lanthanide element, or protonated nitrogen base, having a valence;
$x=1/m$, m being the valence of $R_e$;
u is an integer in a range of 1 to 6, and
wherein a ratio of weight of the polar solvent to total weight of the phosphinic acid or alkali metal salt of phosphinic acid and the molecular weight modifier is 4.0 to 6.0, a molar ratio of the molecular weight modifier to the phosphinic acid or alkali metal salt of phosphoric acid is 0.4 to 9.0; and
wherein the free radical initiator is 0.5% to 13% weight percentage of the phosphinic acid or alkali metal salt of phosphinic acid;
molar amount of the metallic compound or the protonated nitrogen base is a molar amount of the phosphinic acid or alkali metal salt of phosphoric acid divided by m, m being a valence of metal cation of the metallic compound or cation of the protonated nitrogen base; and
the metallic compound is a compound of an alkali metal, alkaline earth metal, transition metal, poor metal, metalloid, or lanthanide element.

2. The process as claimed in claim 1, wherein the alkyne is acetylene.

3. The process as claimed in claim 1, wherein the molecular weight modifier has a formula of

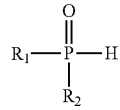

wherein $R_1$ is an alkyl of $C_1$-$C_6$, aryl, alkoxy of $C_1$-$C_6$, phenoxyl, hydroxyalkyl of $C_1$-$C_6$, hydroxyl, or hydroxyl sodium group;
$R_2$ is an alkyl of $C_1$-$C_6$, aryl, alkoxy of $C_1$-$C_6$, phenoxyl, hydroxyalkyl of $C_1$-$C_6$, hydroxyl, or hydroxyl sodium group;
$R_1$ and $R_2$ are not an alkoxy of $C_1$-$C_6$, hydroxyalkyl of $C_1$-$C_6$, hydroxyl, or hydroxyl sodium group at same time.

4. The process as claimed in claim 1, wherein the polar solvent is water, carboxylic acids, or alcohol.

5. The process as claimed in claim 1, wherein the metallic compound is an oxide, hydroxide, hydroxide oxide, sulfate, acetic acid salt, nitrate, chloride, or alcoholate.

6. The process as claimed in claim 1, wherein the alkali metal is Li, Na, or K; the alkaline earth metal is Mg, Ca, or Sr; the transition metal is Ti, Fe, Zr, Zn, or Mn; the poor metal is Al, Sn, or Bi; the metalloid is Sb or Ge; and the lanthanide element is Ce or La.

7. The process as claimed in claim 1, wherein the free radical initiator is an azo compound that is a cationic, anionic, or non-ionic azo compound, inorganic peroxide free radical initiator, or organic peroxide free radical initiator.

* * * * *